United States Patent [19]

White

[11] 4,338,328

[45] Jul. 6, 1982

[54] SULPHOXIDES OF HETEROCYCLICTHIOALKYLTHIOUREAS, UREAS AND GUANIDINES

[75] Inventor: George R. White, Harpenden, England

[73] Assignee: SmithKline & French Laboratories Limited, Welwyn Garden City, England

[21] Appl. No.: 197,430

[22] Filed: Oct. 16, 1980

Related U.S. Application Data

[62] Division of Ser. No. 960,364, Nov. 13, 1978, Pat. No. 4,255,425, which is a division of Ser. No. 824,121, Aug. 12, 1977, Pat. No. 4,140,783, which is a division of Ser. No. 689,013, May 24, 1976, Pat. No. 4,056,620, which is a division of Ser. No. 627,41 8, Oct. 30, 1975, Pat. No. 3,979,398, which is a division of Ser. No. 436,285, Jan. 24, 1974, Pat. No. 3,932,443.

[30] Foreign Application Priority Data

Feb. 8, 1973 [GB] United Kingdom .................. 6153/73
Oct. 23, 1973 [GB] United Kingdom ............... 49257/73

[51] Int. Cl.$^3$ .................... A61K 31/41; C07D 231/12; C07D 249/08; C07D 285/12

[52] U.S. Cl. .................................. 424/269; 548/136; 548/138; 548/141; 548/265; 548/266; 548/267; 548/269; 548/375; 548/377; 548/378; 424/270; 424/273 P

[58] Field of Search ............... 548/138, 136, 141, 262, 548/263, 266, 267, 378, 375, 376, 377, 269; 424/270, 273 P, 269

[56] References Cited

U.S. PATENT DOCUMENTS

| | | | |
|---|---|---|---|
| 3,897,444 | 3/1981 | Durant et al. | 544/224 |
| 3,932,443 | 1/1976 | White | 544/336 |
| 3,950,333 | 4/1976 | Durant et al. | 544/224 |
| 3,950,353 | 4/1976 | Durant et al. | 544/224 |
| 3,979,398 | 9/1976 | White | 548/321 |
| 4,000,296 | 12/1976 | Durant et al. | 544/224 |
| 4,022,797 | 5/1977 | Durant et al. | 548/193 |
| 4,140,783 | 2/1979 | White | 544/336 |

*Primary Examiner*—Alton D. Rollins
*Attorney, Agent, or Firm*—Joan S. Keps; Richard D. Foggio; Alan D. Lourie

[57] ABSTRACT

The compounds are sulphoxides of heterocyclicthioalkylthioureas, ureas and guanidines which are useful to produce inhibition of histamine H-2 receptors.

7 Claims, No Drawings

SULPHOXIDES OF HETEROCYCLICTHIOALKYLTHIOUREAS, UREAS AND GUANIDINES

This is a division of application Ser. No. 960,364 filed Nov. 13, 1978, now U.S. Pat. No. 4,255,425 which is a division of application Ser. No. 824,121 filed Aug. 12, 1977, now U.S. Pat. No. 4,140,783, which is a division of application Ser. No. 689,013 filed May 24, 1976, now U.S. Pat. No. 4,056,620, which is a division of application Ser. No. 627,418 filed Oct. 30, 1975, now U.S. Pat. No. 3,979,398, which is a division of application Ser. No. 436,285 filed Jan. 24, 1974, now U.S. Pat. No. 3,932,443.

This invention relates to sulphoxides, to processes for their preparation and to pharmaceutical compositions comprising them. The sulphoxides of the invention can exist as the addition salt with an acid but, for convenience reference will be made throughout this specification to the parent compounds.

Histamine H-2 receptor antagonists have been defined by Black et al. (Nature 1972, 236, 385) as those compounds which inhibit certain actions of histamine which are not inhibited by the class of substances such as mepyramines which have been commonly called "antihistamines" and which may now be referred to as histamine H-1 receptor antagonists.

Our U.K. Specification No. 1,338,169 describes, inter alia, thioether compounds which are useful as histamine H-2 receptor antagonists and it is with the sulphoxides of certain of these compounds that the present invention is concerned.

According to the present invention we provide sulphoxides of the following structural formula I:

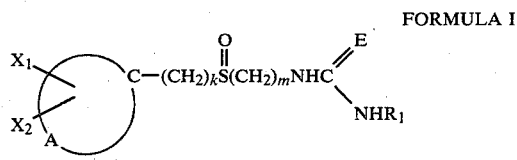

FORMULA I wherein A is such that there is formed with the carbon atom shown an unsaturated heterocyclic nucleus, preferably having five or six atoms, which nucleus comprises at least one nitrogen atom and may comprise further hereto atoms such as sulphur and oxygen e.g. imidazole, pyridine, thiazole, isothiazole, oxazole, isoxazole, pyrazole, triazole, thiadiazole, pyrimidine, pyrazine or pyridazine; $X_1$ and $X_2$ which may be the same or different are hydrogen, lower alkyl, trifluoromethyl, hydroxyl, halogen, amino, or $X_1$ may with $X_2$ and at least two of the atoms comprising A form a further ring e.g. a benzene ring, a pyrimidine ring or a partially unsaturated ring; k is 0 to 2 and m is 2 to 3 provided that the sum of k and m is 3 or 4; E is oxygen, sulphur or $NR_2$; $R_1$ is hydrogen, lower alkyl such as methyl, acyl e.g. benzoyl or dialkylaminoalkyl e.g. dimethylaminoethyl; and $R_2$ is hydrogen, nitro, cyano, alkanesulphonyl or arenesulphonyl.

Preferably A is such that it forms with the carbon atom shown an imidazole, thiazole or pyridine ring. Preferably $X_1$ is hydrogen, methyl, bromine, amino or hydroxyl and $X_2$ is hydrogen. Preferably k is from 1 to 2 and m is 2 or 3 and particularly useful compounds are those wherein k is 1 and m is 2. Preferably E is sulphur or $NR_2$ wherein $R_2$ is cyano. Preferably $R_1$ is methyl.

Particularly useful compounds which are within the scope of the present invention are (5-methyl-4-imidazolyl)methyl 2-(N'-methylthioureido) ethyl sulphoxide and N-cyano-N'-methyl-N'''-[2-((4-methyl-5-imidazolyl) methylsulphinyl)ethyl]guanidine.

The compounds of the present invention may be prepared from amines of the following formula II:

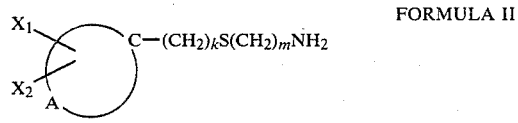

FORMULA II wherein A, $X_1$, $X_2$, k and m have the same significance as in the substance of formula I, by treatment with an oxidising agent such as perbenzoic or peracetic acid or, preferably, with periodate e.g. sodium periodate. This results in the production of a compound of formula III

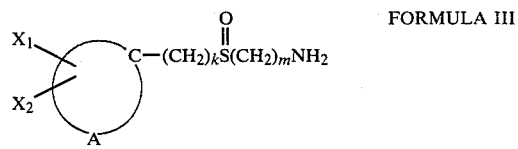

FORMULA III wherein A, $X_1$, $X_2$, k and m have the same significance as in the substance of formula I, which may be isolated or which may be further reacted, without isolation, with an appropriate reactant to yield the required compound of formula I.

The compounds of Formula I where $R_1$ is lower alkyl and E is sulphur may be prepared from the amine of Formula III by reaction with an isothiocyanic ester of Formula $R_1$—N=C=S is an appropriate solvent such as chloroform, ethanol, isopropanol, acetonitrile or water Compounds of Formula I wherein E is oxygen may be formed from the amine of Formula III by treatment thereof with an isocyanate of Formula $R_1NCO$ wherein $R_1$ is lower alkyl. The compounds of Formula I wherein E is oxygen and $R_1$ is hydrogen may be obtained by reaction of the said amines with sodium or potassium cyanate.

Compounds of Formula I wherein E is $NR_2$ may be prepared from the amine of Formula III by treatment thereof with an isothiourea of Formula IV.

FORMULA IV wherein $R_1$ has the same significance as in Formula I. In the case where $R_2$ is cyano, the amine of formula III may be treated with a dialkyldithiocyanimidocarbonate or dialkylcyanimidocarbonate of formula V

$(R_3Y)_2C=N-CN$   FORMULA V wherein $R_3$ is lower alkyl, preferably methyl and Y is sulphur or oxygen, preferably sulphur to yield a compound of formula VI

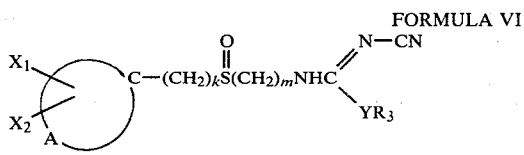
FORMULA VI wherein A, $X_1$, $X_2$, k and m have the same significance as in formula I and $R_3$ and Y have significance as in formula V. Treatment of the substance of formula VI with an amine of formula $R_1NH_2$ wherein $R_1$ is hydrogen, lower alkyl or aralkyl yields the required compound of formula I.

The amines of Formula II may be produced by the processes described in our U.K. Specification No. 1,338,169 namely from a substance of Formula VII

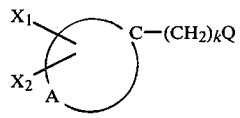
FORMULA VII wherein A, $X_1$, $X_2$ and k have the same significance as in the substance of Formula I; and Q is hydroxyl, halogen or methoxy. In the first stage of these processes, the compound of Formula VII is reacted with an aminomercaptan of the following Formula VIII

Hs—(CH$_2$)$_m$NH$_2$   FORMULA VIII wherein m has the same significance as in Formula I. When Q is halogen, this reaction may be carried out under strongly basic conditions, for example in the presence of sodium ethoxide or sodium hydroxide. Since the substance of Formula VII is a primary amine, it may be necessary to protect the amino group, for example by a phthalmido group which may subsequently be removed by acid hydrolysis or hydrazinolysis. When Q is hydroxyl or halogen it is found that the reaction will take place under acidic conditions e.g. in the presence of a halogen acid such as 48% aqueous hydrogen bromide, or a halogen acid in the presence of glacial acetic acid. When Q is methoxy, the reaction will also take place in the presence of 48% hydrogen bromide.

In an alternative method for the production of our sulphoxide compounds, which is particularly suitable when E is oxygen or N-cyano, the corresponding thioether compound of formula IX:

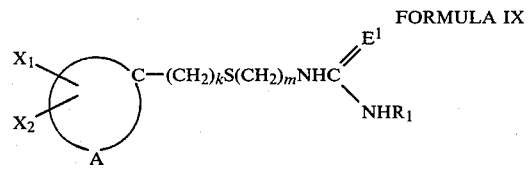
FORMULA IX wherein A, $X_1$, $X_2$, k, m and $R_1$ have the same significance as in Formula I and $E^1$ is oxygen or N-cyano, is treated with an oxidising agent such as perbenzoic or peracetic acid or, preferably, with periodate e.g. sodium periodate. The reaction may conveniently be carried out in a suitable solvent e.g. water.

It will be appreciated that whichever of the above methods is used, an essential step in the process is the treatment of a thioether compound of formula X.

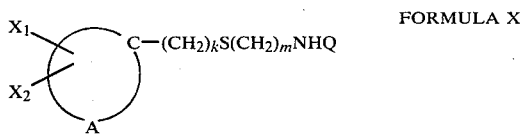
FORMULA X wherein A, $X_1$, $X_2$, k and m have the same significance as in Formula I and Q is hydrogen or

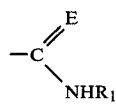

wherein E and $R_1$ have the same significance as in Formula I, with an oxidising agent of the type mentioned hereinbefore.

The sulphoxides of the present invention find their utility in the inhibition of histamine H-2 receptors in the animal body. Although we do not wish to be limited in any way by the following explanation of this utility, we believe that this is largely due to the metabolic reductive conversion of the sulphoxides to the corresponding thioether compounds which are of course, as stated above, highly effective as histamine H-2 receptor antagonists. This conversion is thought to occur in the large intestine of the animal where the active reducing agent is probably present in the intestinal bacterial flora. Because of this mechanism the principle H-2 antagonism action may be delayed for some considerable time after the administration to the animal of the sulphoxides. This is a particularly useful effect in many cases and may be utilized, for example to provide a continuing supply of antagonist to the animal after the effects of an initial dose e.g., of a compound of the type described in U.K. Specification No. 1,338,169 has started to decline. In this regard it is of course possible to administer the sulphoxides of the present invention at the same time and possibly in combination with the said initial dose.

In support of the above explanation of the histamine H-2 receptor inhibition resulting from the administration to animals of the sulphoxides according to the present invention it has been shown that, after oral administration of the sulphoxide, for example to rats at 300 mg/kg orally, the corresponding thioether reduction product can be detected in body fluids e.g., urine and furthermore that incubation of the sulphoxide with rat, dog or human faecal homogenates results in substantial reduction to the corresponding thioether. Thus, the compounds of this invention produce histamine H-2 receptor inhibition in rats at the dose stated above. Inhibitors of histamine H-2 receptors are useful, for example, as inhibitors of gastric acid secretion.

In addition to the above, certain of the sulphoxides of the present invention show activity as histamine H-2 receptor antagonists on the various tests which, as described by Black et. al. (Nature 1972, 236, 387), characterise this activity. For example, they inhibit the histamine stimulated increase in the contraction frequency of isolated guinea pig atrium in oxygenated McEwen's solution at 34° C. As explained by Black et. al (Nature, 1972, 236, 387) this effect can be quantified in terms of the displacement of the dose-response curves wherein the log of the molar concentration of histamine required to produce a response up to a maximum is plotted against the response (expressed as a percentage of the maximum). When competitive antagonism occurs, a series of parallel sigmoid curves are obtained corresponding to different concentrations of antagonist and, from these data, the apparent dissociation constant ($K_B$) for the antagonist-receptor interaction can be calculated. Certain of the sulphoxides of Formula I exhibit the typical characteristics of a competitive antagonist in this test, for example (5-methyl-4-imidazolyl)methyl 2-($N^1$-methylthioureido)sulphoxide which has a $K_B$ of the order of 10 micromolar.

The compounds of Formula I may be combined with a pharmaceutically acceptable carrier to form pharmaceutical compositions.

Advantageously the compositions will be made up in an appropriate dosage form. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Other pharmacologically active compounds may in certain cases be included in the pharmaceutical compositions, for example as mentioned above, a thioether compound which may or may not be exact analogue of the sulphoxide, may be included.

A wide variety of pharmaceutical forms can be employed; thus if a solid carrier is used, the preparation can be tableted, placed in a hard gelatin capsule in powder or pellet form, or in the form of a troche or lozenge. The amount of solid carrier will vary widely but preferably will be from about 25 mg to about 1 gm. If a liquid carrier is used, the preparation may be in the form of a syrup, emulsion, soft gelatin capsule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an amount such that effective inhibition of H-2 histamine receptors is eventually achieved. The route of administration should be such that the sulphoxide can eventually reach the large intestine and is thus preferably orally.

For therapeutic use, the compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric, picric and maleic acids and the addition salt with one of these acids may readily be converted to that with another. Such conversion may be effected by means of ion-exchange techniques. A particularly useful method which also in many cases effects purification to a sufficient degree to allow the resultant solution of the addition salt to be used for pharmacological estimations involves the formation of the picrate salt and conversion therefrom to the chloride salt.

The invention is illustrated but in no way limited by the following examples:

EXAMPLE 1

Preparation of (5-Methylimidazol-4-yl)methyl 2-($N'$-methylthioureido)ethyl sulphoxide (i) A solution of 4-hydroxymethyl-5-methylimidazole hydrochloride (30 g) and cysteamine hydrochloride (23 g) in acetic acid (200 ml) was heated under reflux for 10 hours. Following cooling to 15°–20° C., the solid which crystallised was collected and washed with isopropyl alcohol to give 2[(5-methylimidazol-4-yl)methyl]thioethylamine dihydrochloride (45.5 g), m.p. 189°–192° C.

(ii) 2[5-Methylimidazol-4-yl)methyl]thioethylamine dihydrochloride (14.5 g, 0.06 ml) was added in two portions to a stirred solution of sodium metaperiodate (13.5 g, 0.063 mol) in water (126 ml) kept at 2°–5° C., stirred at this temperature for 3 hours and then left overnight at 0° C. The solid was filtered off and washed with methanol and the combined filtrate and washings (which had deposited more solid which was filtered again) were basified to pH 9.10 by addition of potassium carbonate (15 g) and evaporated to dryness under reduced pressure at 70° with azeotroping with n-propanol. Extraction of the residue with isopropanol and evaporation of the filtered extracts gave crude (5-methylimidazol-4-yl)methyl 2-aminoethyl sulphoxide as an oil. (The infra red spectrum indicated SO absorption at 1020, 1040 $cm^{-1}$).

(iii) This oil was dissolved in ethanol (250 ml) containing 3 drops water and methyl isothiocyanate (5.1 g, 0.07 mol) was added. The solution was left at room temperature overnight, by which time thin-layer chromatography (silica-gel plate; ethyl acetate/methanol-/ammonium hydroxide (5:1:1); visualised by UV and potassium iodoplatinate) indicated complete disappearance of amine, and product formed (white spot K.I.P. initially mauve). Purification by chromatography on silica gel and crystallisation in acetonitrile gave, after final crystallisation from methanol-ether, (5-Methylimidazol-4-yl)methyl-2($N'$-methylthioureido)ethyl sulphoxide (7.1 g,) m.p. 135°–7° C. An analytical sample after a further recrystallisation had m.p. 139°–140° C. Found: C,41.39; H, 6.35; N, 21.39 $C_9H_{16}N_4OS_2$ requires: C, 41.51; H, 6.19; N, 21.52;

EXAMPLE 2

Preparation of N-Cyano-$N'$-methyl-$N''$-[2-((4-methyl-5-imidazolyl)-methyl sulphinyl)ethyl]guanidine Sodium metaperiodate (1.85 g, 8.68 m.mol.) was added to a stirred, cooled (5°) solution of N-cyano-$N'$-methyl-$N''$-[2-((4-methyl-5-imidazolyl)methylthio)ethyl]guanidine (2.085 g, 8.27 m.mol.) in water (83 ml). After 90 minutes stirring at 5° thin layer chromatography indicated almost complete disappearance of starting material. The solution was allowed to stand overnight at room temperature to complete the reaction, then evaporated under reduced pressure to dryness, with azeotroping with n-propanol. The residue was boiled with isopropanol (60 ml), filtered hot, and the filtrate was evaporated to dryness to give the crude product as a glass. This was purified by charcoaling in methanol (40 ml), filtration and dilution with ether to 1500 ml. The liquid was decanted from the flocculent precipitated glass which was kept under a further 1500 ml ether to become semicrystalline, then filtered and allowed to stand overnight in air. The hardened glass was stirred with cold methanol (25 ml) filtered from insoluble crude product and and inorganics (0.28 g. m.p. 190°) and to the filtrate was carefully added ether (to 500 ml) so that two layers formed. On standing undisturbed for three days there separated off white crystals of N-cyano-N'-methyl-N''-[2-((4-methyl-5-imidazolyl)methylsulphinyl)ethyl]guanidine (1.55 g), m.p. 185°–186.5° C. Found: C,44.57; H,6.08; N, 31.18; S,11.91% $C_{10}H_{16}N_6OS$ requires C, 44.76; H, 6.01; N,31.32; S,11.95%.

EXAMPLE 3

Preparation of N-Cyano-N'-methyl-N''-[2-((2-thiazolyl)methylsulphinyl)ethyl]guanidine.

Sodium metaperiodate (220 mg, 1.03 m.mol) was added to a stirred solution of N-cyano-N'-methyl-N''-[2-((2-thiazolyl)methylthio)ethyl]guanidine (255 mg, 1.0 m.mol) in water (90 ml). After 1 hour at 25° then 17 hours at 5° t.l.c. indicated the reaction was essentially complete. The solution was evaporated under reduced pressure at 60° to dryness, with azeotroping with n-propanol (2x). The residue was boiled with isopropanol (20 ml) for 3 minutes, filtered hot from 205 mg of inorganic salts, (100%), and evaporated under reduced pressure to a clear glass which was stirred continuously for 4 days under ether to give crude product (273 mg, 100%) m.p. 110° (softens only). Purification was effected by dissolution in acetonitrile (15 ml) and dilution of the filtered warm solution with ether to 220 ml. After 17 hours standing the precipitate had crystallised yielding, after filtration and washing with ether, N-cyano-N'-methyl-N''-[2-((2-thiazolyl)methylsulphinyl)ethyl]-guanidine, (335 mg), m.p. 112°–113° C. Found: C, 39.62; H, 5.03; N, 25.64%. $C_9H_{13}N_5OS_2$ requires: C, 39.83; H, 4.83; N, 25.81%.

EXAMPLE 4

Treatment of (5-methylimidazol-4-yl)methyl 2-aminoethyl sulphoxide according to the method of Example 1 (iii) with the following compounds:
(a) ethyl isothiocyanate
(b) 2-(dimethylamino)ethyl isothiocyanate
(c) S-methylisothiourea
(d) S-methyl-N-nitroisothiourea
(e) benzoyl isothiocyanate
yielded the following compounds:
(a) (5-methylimidazol-4-yl)methyl 2-(N'-ethylthioureido)ethyl sulphoxide
(b) (5-methylimidazol-4-yl)methyl 2-[N'-2-(dimethylamino)ethyl ureido]ethyl sulphoxide
(c) (5-methylimidazol-4-yl)methyl 2-guanidinoethyl sulphoxide)
(d) (5-methylimidazol-4-yl)methyl 2-(N'-nitroguanidino)ethyl sulphoxide
(e) (5-methylimidazol-4-yl)methyl 2-(N'-benzoylthioureido)ethyl sulphoxide Alkaline hydrolysis with aqueous potassium carbonate of the last mentioned sulphoxide yielded
(f) (5-methylimidazol-4-yl)methyl 2-thioureidoethyl sulphoxide.

EXAMPLE 5

By subjecting the following amino compounds to the reactions described in Example 1 (ii) and 1 (iii):
(a) 2-[(imidazol-4-yl)methyl]thioethylamine
(b) 2-[(5-ethylimidazol-4-yl)methyl]thioethylamine
(c) 2-[(5-isopropylimidazol-4-yl)methyl]thioethylamine
(d) 2-[(5-benzylimidazol-4-yl)methyl]thioethylamine
(e) 2-[(5-bromoimidazol-4-yl)methyl]thioethylamine
(f) 2-[(2-methylimidazol-4-yl)methyl]thioethylamine
(g) 2-[(imidazol-2-yl)methyl]thioethylamine
(h) 2-[(1,5-dimethylimidazol-2-yl)methyl]thioethylamine
(i) 2-[(1-methyl-5-chloroimidazol-2-yl)methyl]thioethylamine
(j) 2-[(3-1,2,4-triazol-3-yl)methyl]thioethylamine
(k) 2-[(pyrazol-3-yl)methyl]thioethylamine
(l) 2-[(pyrid-2-yl)methyl]thioethylamine
(m) 2-[(3-hydroxypyrid-2-yl)methyl]thioethylamine
(n) 2-[(pyridazin-3-yl)methyl]thioethylamine
(o) 2-[(5-amino-1,3,4-thiadiazol-2-yl)methyl]thioethylamine
(p) 2-[(5-trifluoromethylimidazol-4-yl)methyl]thioethylamine
(q) 2-[(pyrimidin-2-yl)methyl]thioethylamine
(r) 2-[pyrazin-2-yl)methyl]thioethylamine
(s) 2-[(2-aminothiazol-3-yl)methyl]thioethylamine
(t) 2-[(isothiazol-3-yl)methyl]thioethylamine
(u) 2-[(4-bromoisothiazol-3-yl)methyl]thioethylamine
(v) 2-[(3-aminopyrid-2-yl)methyl]thioethylamine
(w) 3-[(imidazol-4-yl)methyl]thiopropylamine
(x) 2-[2-(imidazol-4-yl)ethyl]thioethylamine
(y) 2-[(benzimidazol-2-yl)methyl]thioethylamine the following sulphoxides may be produced:
(a) (imidazol-4-yl)methyl 2-(N'-methylthioureido)ethyl sulphoxide
(b) (5-ethylimidazol-4-yl)methyl 2-(N'-methylthioureido)ethyl sulphoxide
(c) (5-isopropylimidazol-4-yl)methyl 2-(N'-methylthioureido)ethyl sulphoxide
(d) (5-benzylimidazol-4-yl)methyl 2-(N'-methylthioureido)ethyl sulphoxide
(e) (5-bromoimidazol-4yl)methyl 2-(N'-methylthioureido)ethyl sulphoxide
(f) (2-methylimidazol-4-yl)methyl 2-(N'-methylthioureido)ethyl sulphoxide
(g) (imidazol-2-yl)methyl 2-(N'-methylthioureido)ethyl sulphoxide
(h) (1,5-dimethylimidazol-2-yl)methyl 2-(N'-methylthioureido)ethyl sulphoxide
(i) (1-methyl-5-chloroimidazol-2-yl)methyl 2-(N'-methylthioureido)ethyl sulphoxide
(j) (3-1,2,4-triazol-3yl)methyl 2-(N'-methylthioureido)ethyl sulphoxide
(k) (pyrazol-3-yl)methyl 2-(N'-methylthioureido)ethyl sulphoxide
(l) (pyrid-2-yl)methyl 2-(N'-methylthioureido)ethyl sulphoxide
(m) (3-hydroxypyrid-2-yl)methyl 2-(N'-methylthioureido)ethyl sulphoxide
(n) (pyridazin-3-yl)methyl 2-(N'-methylthioureido)ethyl sulphoxide
(o) (5-amino-1,3,4-thiadiazol-2-yl)methyl 2-(N'-methylthioureido)ethyl sulphoxide
(p) (5-trifluoromethylimidazol-4-yl)methyl 2-(N'-methylthioureido)ethyl sulphoxide
(q) (pyrimidin-2-yl)methyl 2-(N'-methylthioureido)ethyl sulphoxide
(r) (pyrazin-2-yl)methyl 2-(N'-methylthioureido)ethyl sulphoxide
(s) (2-aminothiazol-3-yl)methyl 2-(N'-methylthioureido)ethyl sulphoxide (t) (isothiazol-3-yl)methyl 2-(N'-methylthioureido)ethyl sulphoxide
(u) (4-bromoisothiazol-3-yl)methyl 2-(N'-methylthioureido)ethyl sulphoxide
(v) (3-aminopyrid-2-yl)methyl 2-(N'-methylthioureido)ethyl sulphoxide
(w) (imidazol-4-yl)methyl 3-(N'-methylthioureido)propyl sulphoxide
(x) 2-(imidazol-4-yl)ethyl 2-(N'-methylthioureido)ethyl sulphoxide
(y) (benzimidazol-2-yl)methyl 2-(N'-methylthioureido)ethyl sulphoxide

EXAMPLE 6

Periodate oxidation of the following compounds by the procedure described in Example 2.
  (a) N-cyano-N'-ethyl-N''-[2-((4-methyl-5-imidazolyl)methylthio)ethyl]guanidine
  (b) N-cyano-N'-methyl-N''-[2-((3-hydroxy-2-pyridyl)methylthio)ethyl]guanidine
  (c) N-cyano-N'-methyl-N''-[2-((4-bromo-5-imidazolyl)methylthio)ethyl]guanidine
  (d) N-cyano-N'-methyl-N''-[3-((4-methyl-5-imidazolyl)methylthio)propyl]guanidine
  (e) N-cyano-N'-methyl-N''-[2-((3-isothiazolyl)methylthio)ethyl]guanidine
  (f) N-cyano-N'-methyl-N''-[2-((3-bromo-2-pyridyl)methylthio)ethyl]guanidine
  (g) N-methyl-N'-[2-((4-methyl-5-imidazolyl)methylthio)ethyl]urea.
  (h) N-methyl-N'-[2-((2-pyridyl)methylthio)ethyl]urea
led to the production of the following compounds:
  (a) N-cyano-N'-ethyl-N''-[2-((4-methyl-5-imidazolyl)methylsulphinyl)ethyl]guanidine
  (b) N-cyano-N'-methyl-N''-[2-((3-hydroxy-2-pyridyl)methylsulphinyl)ethyl]guanidine
  (c) N-cyano-N'-methyl-N''-[2-((4-bromo-5-imidazolyl)methylsulphinyl)ethyl]guanidine
  (d) N-cyano-N'-methyl-N''-[3-((4-methyl-5-imidazolyl)methylsulphinyl)propyl]guanidine
  (e) N-cyano-N'-methyl-N''-[2-((3-isothiazolyl)methylsulphinyl)ethyl]guanidine
  (f) N-cyano-N'-methyl-N''-[2-((3-bromo-2-pyridyl)methylsulphinyl)ethyl]guanidine
  (g) N-methyl-N'-[2-((4-methyl-5-imidazolyl)methylsulphinyl)ethyl]urea
  (h) N-methyl-N'-[2-((2-pyridyl)methylsulphinyl)ethyl]urea

EXAMPLE 7

Treatment of (5-methylimidazol-4-yl)methyl 2-aminoethyl sulphoxide under reflux conditions in acetonitrile with the following isothioureas:
  (a) N-benzenesulphonyl-S-methylisothiourea
  (b) N-(4-chlorobenzenesulphonyl)-S-methylisothiourea
  (c) N-methanesulphonyl-S-methylisothiourea
  (d) N-n-propanesulphonyl-S-methylisothiourea
  (e) N-p-toluenesulphonyl-S-methylisothiourea
and isolation and recrystallisation of the product yielded:
  (a) N-benzenesulphonyl-N'-methyl-N''-2-((4-methyl-5-imidazolyl)methylsulphinyl)ethyl guanidine
  (b) N-(4-chlorobenzenesulphonyl)-N'-methyl-N''-2-((4-methyl-5-imidazolyl)methylsulphinyl)ethyl guanidine
  (c) N-methanesulphonyl-N'-methyl-N''-2-((4-methyl-5-imidazolyl)methylsulphinyl)ethyl guanidine
  (d) N-n-propanesulphonyl-N'-methyl-N''-2-((4-methyl-5-imidazolyl)methylsulphinyl)ethyl guanidine
  (e) N-p-toluenesulphonyl-N'-methyl-N''-2-((4-methyl-5-imidazolyl)methylsulphinyl)ethyl guanidine

EXAMPLE 8

| Ingredients | Amounts |
| --- | --- |
| (5-Methylimidazol-4-yl)methyl 2-(N'-methylthioureido)ethyl sulphoxide | 150 mg |
| Sucrose | 75 mg |
| Starch | 25 mg |
| Talc | 5 mg |
| Stearic Acid | 2 mg |

The ingredients are screened, mixed and filled into a hard gelatin capsule.

EXAMPLE 9

| | |
| --- | --- |
| N-Cyano-N'-methyl-N''-[2-((4-methyl-5-imidazolyl)methylsuphinyl)ethyl]guanidine | 200 mg |
| Lactose | 100 mg |

The ingredients are screened, mixed and filled into a hard gelatin capsule.

What we claim is:
1. A compound of the formula:

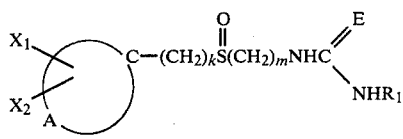

wherein A is such that the heterocyclic nucleus formed is a pyrazole, 1,2,4-triazole or 1,3,4-thiadiazole ring; $X_1$ and $X_2$, which may be the same or different, are hydrogen, lower alkyl, trifluoromethyl, hydroxyl, halogen or amino; k is 0 to 2 and m is 2 or 3 provided that the sum of k and m is 3 or 4; E is oxygen, sulphur or $NR_2$; $R_1$ is hydrogen, lower alkyl, benzoyl or dimethylaminoethyl; and $R_2$ is hydrogen, nitro, cyano, alkanesulphonyl having 1 to 3 carbon atoms, benzenesulphonyl, halobenzenesulphonyl or toluenesulphonyl.

2. A compound of claim 1 wherein $X_1$ is hydrogen, methyl, bromine, amino or hydroxyl and $X_2$ is hydrogen.

3. A compound of claim 1 wherein k is 1 or 2 and m is 2 or 3.

4. A compound of claim 4 wherein k is 1 and m is 2.

5. A compound of claim 1 wherein E is sulphur or $NR_2$ wherein $R_2$ is cyano.

6. A compound of claim 1 wherein $R_1$ is methyl.

7. A pharmaceutical composition to inhibit histamine H-2 receptors comprising in an amount effective to inhibit said receptors a compound of claim 1 together with a pharmaceutically acceptable diluent or carrier.

* * * * *